(12) United States Patent
Pivetti et al.

(10) Patent No.: US 9,056,818 B2
(45) Date of Patent: Jun. 16, 2015

(54) PROCESS FOR THE PREPARATION OF DERIVATIVES OF 1-(2-HALOBIPHENYL-4-YL)-CYCLOPROPANECARBOXYLIC ACID

(75) Inventors: Fausto Pivetti, Parma (IT); Maria Gioia Fornaretto, Parma (IT); Marco Re, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 436 days.

(21) Appl. No.: 12/846,341

(22) Filed: Jul. 29, 2010

(65) Prior Publication Data

US 2011/0039934 A1 Feb. 17, 2011

(30) Foreign Application Priority Data

Aug. 4, 2009 (EP) ..................... 09167206

(51) Int. Cl.
C07C 61/04 (2006.01)
C07C 253/30 (2006.01)
C07C 51/09 (2006.01)
C07C 253/14 (2006.01)

(52) U.S. Cl.
CPC ............... *C07C 253/30* (2013.01); *C07C 51/09* (2013.01); *C07C 253/14* (2013.01)

(58) Field of Classification Search
CPC ........................................... C07C 61/04
USPC ........................................ 562/405
See application file for complete search history.

(56) References Cited

U.S. PATENT DOCUMENTS 7,662,995 B2 2/2010 Raveglia et al.
2009/0312426 A1 12/2009 Folleas et al.
2010/0099768 A1 4/2010 Raveglia et al.

FOREIGN PATENT DOCUMENTS

WO 2004/074232 9/2004
WO WO-2004074232 * 9/2004

OTHER PUBLICATIONS

U.S. Appl. No. 13/078,039, filed Apr. 1, 2011, Pivetti, et al.
European Search Report in Application No. 091672063.3, issued Jan. 1, 2010.
Peretto et al., *J. Med. Chem.*, vol. 48, (2005) pp. 5705-5720.
U.S. Appl. No. 13/723,662, filed Dec. 21, 2012, Imbimbo.

* cited by examiner

*Primary Examiner* — Yong Chu
*Assistant Examiner* — Sonya Wright
(74) *Attorney, Agent, or Firm* — Oblon, McClelland, Maier & Neustadt, L.L.P.

(57) ABSTRACT

Compounds according to formula (IA):

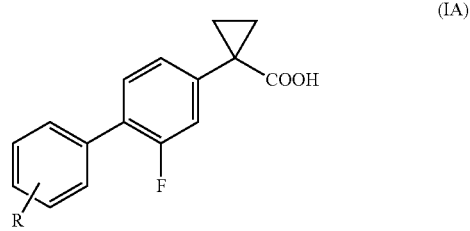

may be efficiently prepared by the disclosed process.

6 Claims, No Drawings

PROCESS FOR THE PREPARATION OF DERIVATIVES OF 1-(2-HALOBIPHENYL-4-YL)-CYCLOPROPANECARBOXYLIC ACID

CROSS REFERENCES TO RELATED APPLICATIONS

This application claims priority to European Patent Application No. 09167206.3, filed on Aug. 4, 2009, which is incorporated herein by reference in its entirety.

BACKGROUND OF THE INVENTION

1. Field of the Invention

The present invention relates to processes for the preparation of compounds of formula (IA):

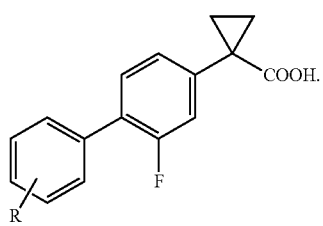

(IA)

Such compounds are useful for prevention and/or treatment of neurodegenerative diseases such as Alzheimer's disease.

2. Discussion of the Background

Alzheimer's disease is a neurodegenerative disorder characterized from a histopathologic point of view by a diffuse presence of extracellular and perivascular neuritic plaques and intracellular neurofibrillary tangles in the cerebral parenchyma of Alzheimer patients. Neuritic plaques are mainly composed of aggregates of a protein with 39-43 amino acid residues known as β-amyloid (βA), and, depending on the numbers of amino acids, $A\beta_{39}$, $A\beta_{40}$, $A\beta_{42}$ and $A\beta_{43}$.

Compounds have been reported which can reduce the production of the most neurotoxic isoform of β-amyloid, namely the form containing 42 amino acids ($A\beta_{42}$), through their interaction with a macromolecular/multiprotein enzymatic complex with aspartyl-protease activity, known as γ-secretase.

WO 2004/074232 discloses derivatives of 1-(2-halobiphenyl-4-yl)-cyclopropanecarboxylic acid of formula (I) capable of modulating γ-secretase activity without affecting other important metabolic processes such as cyclooxygenase-enzymes activity.

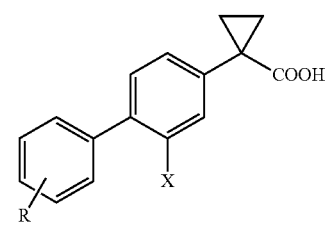

(I)

R is defined below, and X is preferably fluorine.

The key intermediate step in the preparation of said compounds is a Suzuki reaction between a suitable phenylboronic acid or an ester thereof with a 3,4-dihalo-cyclopropanecarboxylic acid, preferably a 3-fluoro-4-halo-cyclopropanecarboxylic acid.

In WO 2004/074232, 3-fluoro-4-halo-cyclopropanecarboxylic acid may be obtained starting from 3-fluoro-4-halotoluene which is transformed into the corresponding benzyl bromide by radical bromination in carbon tetrachloride ($CCl_4$); the resulting bromide is then transformed into the 3-fluoro-4-halophenylacetonitrile; and the latter is reacted with 1,2-dibromoethane to give the corresponding 3-fluoro-4-halo-phenylcyclopropanenitrile, which is finally hydrolyzed to the desired 3-fluoro-4-halo-cyclopropanecarboxylic.

However, the process described in WO 2004/074232 provides a low overall yield (12-14%) and suffers from severe restrictions for the industrial use. In particular, the final Suzuki coupling reaction has a poor yield, and the resulting product is difficult to purify by crystallization without a loss of yield. Silica gel chromatography has been used for such purification, but the scale-up of silica gel chromatography is tedious and requires large volumes of solvents.

Moreover, the radical bromination step used for the preparation of the benzyl bromide derivative gives a significant amount of the bis-halogenated side-product, detrimental to its yield, and involves the use of $CCl_4$ which is highly toxic and also both ozone-depleting and a greenhouse gas.

Thus, there remains a need for a process for producing such compounds which does not suffer from the above-mentioned drawbacks.

SUMMARY OF THE INVENTION

The present invention provides a process for the preparation of derivatives of 1-(2-halobiphenyl-4-yl)-cyclopropanecarboxylic acid of formula (IA), in which the halogen atom is fluorine, and which does not suffer from all the aforementioned drawbacks.

Accordingly, it is one object of the present invention to provide novel methods for producing a compound of formula (IA).

It is another object of the present invention to provide novel methods for producing a compound of formula (IA) which do not suffer from the aforementioned drawbacks.

These and other objects, which will become apparent during the following detailed description, have been achieved by the inventors' discovery that carrying out the Suzuki reaction on the nitrile derivative before the hydrolysis to the corresponding carboxylic acid derivative improves the efficiency of the process.

Moreover, the inventors have also discovered different conditions for improving the yields of the other steps, in particular the radical bromination step.

The process of the present invention is more efficient, especially for large scale production, and provides a higher yield of the compounds of formula (IA) in high chemical purity without the need for a chromatographic purification step.

Thus, the present invention provides:

(1) A process for the preparation of a compound of formula (IA):

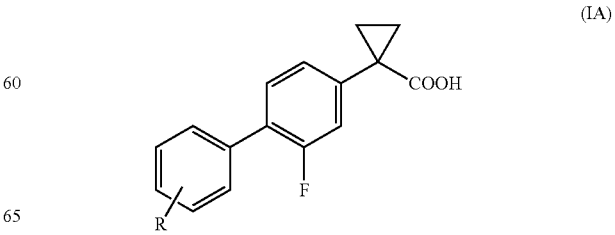

(IA)

wherein R represents one or more groups independently selected from:
halogen atoms, preferably chlorine;
$CF_3$;
$CH=CH_2$;
CN;
$CH_2OH$
$NO_2$;
methylenedioxy;
ethylenedioxy;
cycloalkyl, preferably $C_3$-$C_6$ cycloalkyl;
phenyl;
$OR_1$ or $NHCOR_1$ wherein $R_1$ is selected from $CF_3$, alkenyl, alkynyl, benzyl, and phenyl;
$SR_2$, $SOR_2$ or $COR_2$ wherein $R_2$ is alkyl;
and pharmaceutically acceptable salts thereof,
said process comprising the following steps according to scheme 1:
i) reacting a compound of formula (IV) wherein X' is chlorine, bromine, iodine or a triflate group ($CF_3SO_3$), preferably bromide, with 1,2-dibromoethane to form a compound of formula (V);
ii) coupling a compound of formula (V) with a compound a formula (VI) wherein R is as defined above to form a compound of formula (VII); and
iii) hydrolyzing a compound of formula (VII) to obtain a compound of formula (I).

Preferably, the present invention provides a process for the preparation of a compound of formula (IA) wherein R is chlorine.

More preferably, the present invention provides a process for the preparation of 1-(3',4'-dichloro-2-fluoro[1,1'-biphenyl]-4-yl)-cyclopropanecarboxylic acid of formula:

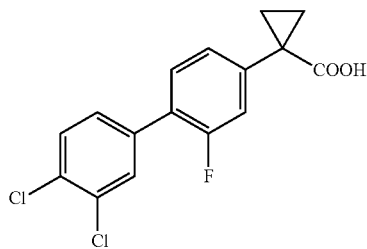

Said compound has also been referred to with the code CHF 5074.

The present invention also provides a process for preparing a pharmaceutical composition, said process comprising steps (i)-(iii) and an additional step comprising admixing of one or more pharmaceutically acceptable excipients.

DETAILED DESCRIPTION OF THE PREFERRED EMBODIMENTS

The term "halogen atoms" includes fluorine, chlorine, bromine, and iodine.

"Alkyl" means straight chain or branched $C_1$-$C_4$ alkyl, such as methyl, ethyl, n-propyl, isopropyl, n-butyl, isobutyl, sec-butyl, tert-butyl, "Alkenyl" means straight chain or branched $C_2$-$C_6$ alkenyl, such as vinyl, 1-propenyl, 2-propenyl, 1-butenyl, isobutenyl, or straight- or branched-pentenyl and hexenyl. The term "alkynyl" is to be construed in an analogous manner.

"Cycloalkyl" means a cyclic non-aromatic hydrocarbon group containing from 3 to 8 carbon atoms. Examples include cyclopropyl, cyclobutyl, cyclopentyl, cyclohexyl and cycloheptyl.

"Saturated heterocyclic" means a saturated heterocyclic group having at least 4 carbon atoms and at least one heteroatom, preferably from one to four heteroatoms selected from nitrogen, oxygen, and sulphur. Examples include piperidyl or tetrahydrofuryl.

The term "pharmaceutically acceptable salts" refer to salts obtained by reacting the main compound, in acid form, with an inorganic or organic base to form a salt approved for human use, e.g., sodium, potassium, calcium, magnesium, and ammonium salts.

The present invention provides a process for the preparation of a compound of formula (IA) wherein R is as defined above.

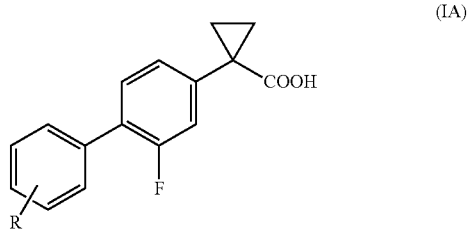

When R is cycloalkyl, it is optionally substituted by one or more groups independently selected from alkyl, $CF_3$, OH and oxo groups. Preferably the cycloalkyl group is $C_3$-$C_6$ cycloalkyl. When R is phenyl, it is optionally substituted by one or more groups independently selected from halogen atoms, $CF_3$, $OCF_3$, OH, alkyl and a saturated heterocyclic. The saturated heterocyclic group is preferably a monocyclic ring having 5 or 6 atoms and one or two nitrogen atoms or one nitrogen atom and one oxygen atom such as pyrrolidine, imidazolidine, and isoxazolidine.

The present process may comprise the steps shown in Scheme 1.

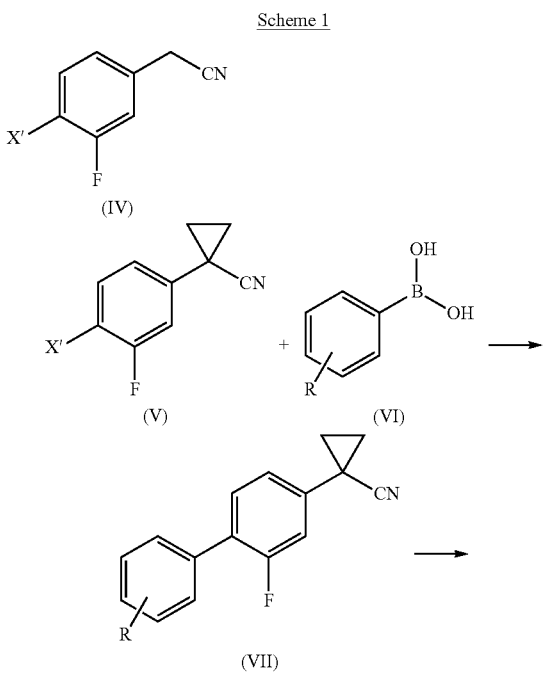

Scheme 1

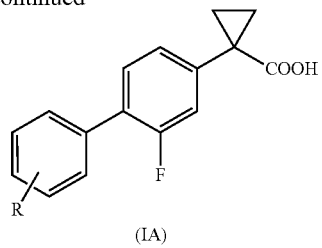

Any compound of formula (IV), with X' selected from the group consisting of chlorine, bromide, iodine and a CF$_3$SO$_3$ group (triflate), which is commercially available, may be used as starting material. Preferably, the compound wherein X' is bromide is used as starting material.

In the first step (step i), the compound of formula (IV) is reacted with 1,2-dibromoethane to form a compound of formula (V) wherein X' is as defined above. Advantageously, step (i) may be conducted in an organic solvent such as ethanol or acetonitrile or mixtures thereof with water.

Preferably, the cyclopropanation step (step (i)) is carried out as a phase transfer catalysis reaction in the presence of concentrated NaOH and tetrabutylammonium chloride (TBAC) or tetrabutylammonium bromide (TBAB). The concentration of NaOH can advantageously range from 30 to 50% w/v.

The temperature in step (i) may be preferably maintained from about 20° C. to about 50° C.

Generally, the compound of formula (V), which is preferably 4-bromo-3-fluorophenylcyclopropanenitrile, is obtained with a yield higher than 80%, preferably equal to or higher than 90%.

Optionally, the obtained compound of formula (V) may be further purified by crystallization before its use in the following step of the process according to standard procedures.

In the second step (step ii), the compound of formula (V), is reacted with a phenyl boronic acid of formula (VI) wherein R represents one or more groups independently selected from halogen atoms, preferably chlorine; CF$_3$; CH=CH$_2$; CN; CH$_2$OH; NO$_2$; methylenedioxy; ethylenedioxy; cycloalkyl; phenyl; OR$_1$ or NHCOR$_1$ wherein R$_1$ is selected from the group consisting of CF$_3$, alkenyl, alkynyl, benzyl, and phenyl; SR$_2$, SOR$_2$ and COR$_2$ wherein R$_2$ is alkyl.

Preferably, the reaction, known as Suzuki reaction or Miyaura-Suzuki reaction, is carried out using 4-bromo-3-fluoro-phenylcyclopropanenitrile as the compound of formula (V) and 3,4-dichloro-phenylboronic acid as the compound of formula (VI).

Said reaction, which employs a palladium catalyst, may also be carried out using an alkyl boronic ester instead of a boronic acid. Advantageously, any palladium catalyst such as, for example, tetrakis(triphenylphosphine)palladium [Pd(PPh$_3$)$_4$], palladium on activated charcoal also known as Palladium on Carbon (Pd/C), palladium on alumina, or a mixture of Pd(OCOCH$_3$)$_2$ and triphenylphosphine, P(Ph)$_3$, may be used as catalyst.

Advantageously, step (ii) may be conducted in the presence of an organic solvent such as ethanol, acetone, tetrahydrofuran (THF), isopropyl alcohol, N-methylpyrrolidone (NMP), dioxane and mixtures thereof with water. A combination of organic solvents may also be used.

Preferably, when Pd(PPh$_3$)$_4$ or a mixture of Pd(OCOCH$_3$)$_2$ and PPh$_3$ is used, the reaction is carried out in the presence of N-methylpyrrolidone (NMP) or a mixture of dioxane/water 2:1. Otherwise, when Pd/C is used, the preferred solvent is ethanol.

Step (ii) is advantageously conducted in the presence of from 1 to 4 equivalents of a base. Bases which may be advantageously used include Na$_2$CO$_3$, K$_2$CO$_3$, K$_3$PO$_4$, Cs$_2$CO$_3$, NaOH, and KOH. The preferred bases are Na$_2$CO$_3$, K$_2$CO$_3$, or K$_3$PO$_4$.

Optionally, additives such as triphenylphosphine (P(Ph$_3$)), polymethylhydrosiloxane (PMHS), tetrabutylammonium bromide (TBAB), 1,4-diazabicyclo[2.2.2]octane (DABCO), or NaI may be added to the reaction medium. Generally, the reaction is carried out at the temperature from 80 to 140° C., preferably at 110°.

Advantageously, step (ii) may be conducted using an equimolar amount of the compound (VI) with respect to compound (V), or with a slight molar excess.

Generally, the compound of formula (VI) is obtained with a yield higher than 60%, preferably higher than 70%, more preferably higher than 80%. The compound of formula (VI) is preferably 3',4'-dichloro-2-fluoro-4-cyanomethyl-biphenyl.

The preferred conditions of step (ii) are:
solvent: NMP;
base: 4 equivalents K$_3$PO$_4$ in powder form;
catalyst: a 1:2 w/w mixture of Pd(OCOCH$_3$)$_2$ and PPh$_3$.
temperature: 110° C.

With these conditions, 3',4'-dichloro-2-fluoro-4-cyanomethyl-biphenyl is obtained with a yield higher than 90%.

Optionally, the obtained compound may be further purified by crystallization before its use in the following step of the process according to standard procedures.

In the third step (step iii), a compound of formula (VII) is hydrolyzed to obtain the desired compound of formula (IA) according to well known methods. Preferably, the hydrolysis is conducted in a mixture of methanol and water in the presence of a strong base, preferably KOH under reflux.

Generally, the compound of formula (IA), which is preferably 1-(3',4'-dichloro-2-fluoro[1,1'-biphenyl]-4-yl)-cyclopropanecarboxylic acid, is obtained with a yield higher than 65%.

The compound of formula (IA) may be washed, filtered and isolated by various well known techniques. Said compound may be further purified by crystallization according to standard procedures and is obtained with a high chemical purity, e.g. higher than 95% without using final purification by chromatography. Crystallization from a mixture of n-heptane and isopropyl alcohol is particularly preferred.

The obtained compound (IA) may be further transformed into a corresponding pharmaceutically acceptable salt according to various known techniques.

In an alternative embodiment, when NMP is used as solvent for the reaction of step (ii), the compound of formula (IA) in the form of an alkaline salt may be obtained by direct precipitation in a basic aqueous solution, without isolation of the intermediate compound (VII). This is possible as it has been found that all the impurities of step (II) do not contain groups than can be salified in the water phase. This allows an increase of the yield of the overall process. The alkaline salt can be converted to the free acid form according to known methods.

The overall yield is generally at least 30%, preferably equal to or higher than 40% more preferably higher than 50%.

In a particular aspect, the process of the present invention may further comprise the steps of preparing the compound (IV) starting from the commercially available compound (II) according to Scheme 2.

Scheme 2

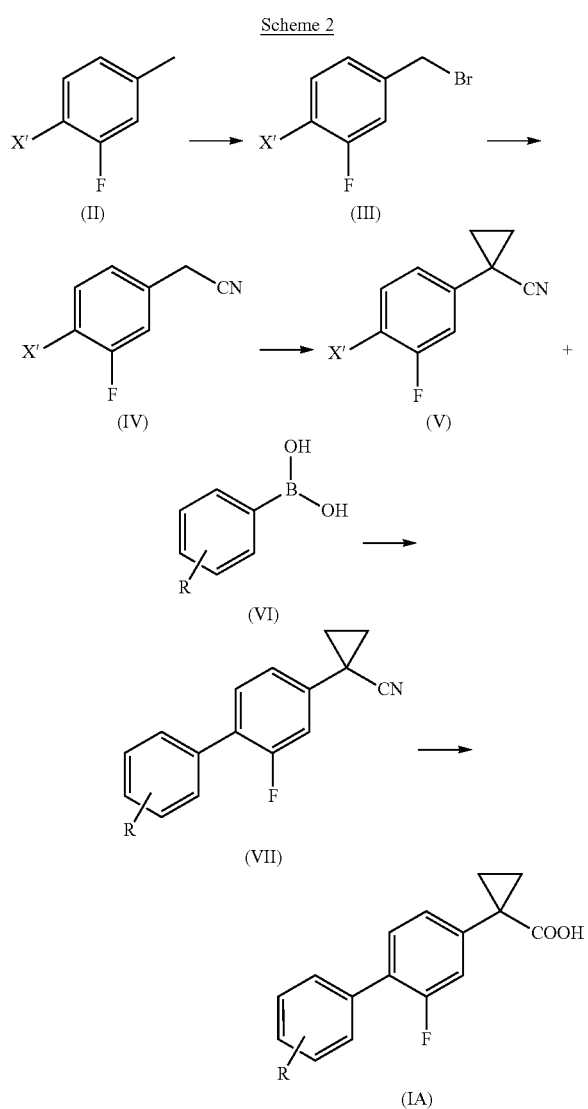

In order to obtain compound (IV), a compound of formula (II), with X' selected from the group consisting of chlorine, bromide, iodine and a CF$_3$SO$_3$— (triflate) group is submitted to radical bromination to form a compound of formula (III). Advantageously the radical bromination is conducted with N-bromosuccinimide (NBS) in the presence of a catalytic amount of benzoyl peroxide [PhCOO)$_2$] and acetonitrile as a solvent. Generally, the reaction is carried out at the solvent reflux temperature.

Preferably, in order to minimize the formation of dibrominated product, the bromination is conducted with a slight excess of NBS, preferably 1.05 mole equivalents to 1 mole equivalents of compound (II), and in the presence of 0.04 equivalents of PhCOOO$_2$.

Generally, the compound of formula (III), which is preferably 3-fluoro-4-bromo-benzyl bromide, is obtained with a yield higher than 85%, preferably higher than 90%.

The compound of formula (III), optionally further purified by crystallization according to standard procedures, is then transformed into the corresponding nitrile derivative of formula (IV) using sodium cyanide or another suitable salt. Advantageously, said transformation is conducted in an organic solvent such as ethanol or acetonitrile, preferably ethanol, keeping the temperature from about 20° C. to about 60° C., preferably between about 40° C. and about 50° C. Preferably, the reaction is conducted with a molar excess of sodium cyanide, advantageously from 1.2 mole equivalent to 1.0 mole equivalent of sodium cyanide, preferably 1.05 mole equivalent to 1 equivalent of compound (III).

Generally, the compound of formula (IV), which is preferably 4-bromo-3-fluoro-benzylnitrile, is obtained with a yield higher than 50%.

Optionally, the obtained compound (IV), before of being subjected to the steps described above may be further purified by crystallization according to standard procedures.

Accordingly, the present invention also provides a process for the preparation of a compound of formula (IA) with R as defined above, and pharmaceutically acceptable salts thereof, said process comprising the following steps according to scheme 2:

i) submitting a compound of formula (II), wherein X' is chlorine, bromine, iodine or a triflate group (CF$_3$SO$_3$), preferably bromide, to radical brominaton to form a compound of formula (III);
ii) transforming the compound of formula (III) into the corresponding nitrile derivative of formula (IV);
iii) reacting a compound of formula (IV) with 1,2-dibromoethane to form a compound of formula (V);
iv) coupling a compound of formula (V) with a compound a formula (VI) wherein R is defined as above, to form a compound of formula (VII); and
v) hydrolyzing a compound of formula (VII) to obtain a compound of formula (IA).

The compounds of formula (IA) obtained by the processes of the invention may be used in the preparation of pharmaceutical compositions for the treatment and/or the prevention of neurodegenerative diseases such as Alzheimer's disease. Said pharmaceutical compositions, preferably for the oral use, comprise at least one compound of formula (IA) in admixture with one or more pharmaceutically acceptable excipients and/or carriers, for example those described in Remington's Pharmaceutical Sciences Handbook, XVII Ed., Mack Pub., N.Y., U.S.A.

Other features of the invention will become apparent in the course of the following descriptions of exemplary embodiments which are given for illustration of the invention and are not intended to be limiting thereof.

EXAMPLES

Example 1

Preparation of 4-bromo-3-fluorobenzyl bromide (III)

A solution of 4-bromo-3-fluorotoluene (21.5 g, 0.114 moles) in acetonitrile (200 ml) is added with N-bromosuccinimide, (NBS; 21.2 g, 0.119 moles). The mixture is refluxed, added with dibenzoyl peroxide (1.4 g, 0.004 moles), refluxed for 3 hour, then cooled at room temperature, and extracted with water. The aqueous phase is discarded, and the organic phase is washed with brine, dried over sodium sulphate, and concentrated under vacuum to give an oil (27.1 g, 90% yield).

Example 2

Preparation of 4-bromo-3-fluorophenylacetonitrile (IV)

A solution of 4-bromo-3-fluorobenzyl bromide (27 g, 0.1 moles) in ethanol (200 ml) is mixed with NaCN (5.4 g, 0.11 moles) and refluxed for 3 hours. The mixture is concentrated under vacuum; the resulting residue is taken up with water and then extracted with ethyl acetate. The organic phase is washed with brine, dried over sodium sulfate, and concentrated under vacuum to give a dark oil (12.1 g, 56% yield).

Example 3

Preparation of 4-bromo-3-fluorophenylcyclopropanenitrile (V)

A solution of 4-bromo-3-fluorophenylacetonitrile (1 g, 4.6 mmoles) in toluene (4 ml) is mixed with 0.6 ml (7 mmoles) of 1,2-dibromoethane, a 50% NaOH aqueous solution (4 ml), and tetrabutylammonium bromide (0.32 g, 1 mmoles). The mixture is kept under stirring at room temperature for 4 hours, then diluted with water and extracted with ethyl acetate. The organic phase is recovered, and the solvent is eliminated under vacuum to give a brown solid, which is subjected to silica gel chromatography purification, to afford an orange to yellow product in the solid form (1 g, yield 90%).

Example 4

Preparation of 1-(3',4'-dichloro-2-fluoro[1,1'-biphenyl]-4-yl)-cyclopropanenitrile (VI)

In a flask in inert atmosphere, 3,4-dichlorophenylboronic acid (374 mg, 1 eq), Pd(OAc)$_2$ (44 mg, 0.1 eq), PPh$_3$ (105 mg, 0.2 eq), and fine mesh K$_3$PO$_4$ (1.6 g, 4 eq) are added to 4-bromo-3-fluorophenylcyclopropanenitrile (470 mg, 1 eq). 5 mL of previously degassed N-methylpyrrolidone (NMP) are added at room temperature. The reaction mixture is heated at 110° C. for 2 hours to reach completion (monitored by $^{19}$F NMR), then diluted with ethyl acetate, and washed with water. The organic phase is recovered, and the solvent evaporated to give a rose-violet powder (700 mg). To the solid, a water:acetone 1:1 v/v mixture (40 ml) is added, and then the suspension is heated to reflux under stirring to obtain a solution. After evaporation of acetone, a solid light violet product is obtained (560 mg, yield 95%).

Example 5

Preparation of 1-(3',4'-dichloro-2-fluoro[1,1'-biphenyl]-4-yl)-cyclopropane carboxylic acid (IA)

1-(3',4'-dichloro-2-fluoro[1,1'-biphenyl]-4-yl)-cyclopropanenitrile (14.3 g, 0.047 mol) is dissolved in a mixture of methanol (143 ml) and water (71.5 ml), potassium hydroxide (35.1 g, 0.563 mol) is added portionwise, and the mixture is refluxed for 48 hours. The reaction mixture is cooled and poured into a solution of aqueous hydrogen chloride 36% (57 ml) in water (57 ml) at 20-25° C. The suspension is stirred and filtered; the solid is repeatedly washed with water and dried at 40° C. under vacuum. The crude product is dissolved in refluxing 2-propanol (178 ml), the solution is mixed with activated carbon (0.3 g), stirred at reflux and filtered, concentrated and mixed with n-heptane (116 ml). The hot solution is cooled to 0 to 5° C. and the crystallized solid is filtered, washed with 2-propanol and dried at 40° C. under vacuum. The compound 1-(3',4'-dichloro-2-fluoro[1,1'-biphenyl]-4-yl)-cyclopropanecarboxylic acid is obtained as a white powder (10.3 g, 68% yield).

HPLC-UV purity (255 nm): 99.8%

$^1$H NMR (DMSO-d6, 300 MHz): 12.51 (bs, 1H); 7.78 (m, 2H); 7.54 (m, 2H); 7.30 (m, 2H); 1.48 (m, 2H); 1.22 (m, 2H)

MS (ESI$^-$, 40 V): 323 (M$^-$); 279.

Melting range: 199-200° C.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for the preparation of 1-(3',4'-dichloro-2-fluoro[1,1'-biphenyl]-4-yl)-cyclopropanecarboxylic acid of formula (IA):

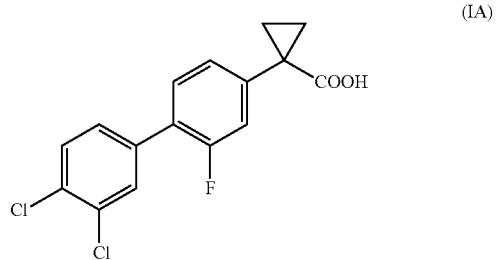 [SMILES: O=C(O)C1(c2ccc(-c3ccc(Cl)c(Cl)c3)c(F)c2)CC1]

said process comprising:

(a) reacting a compound of formula (IV):

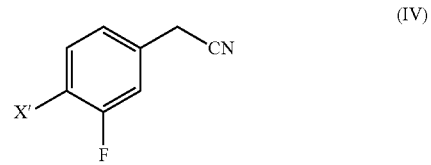

wherein X' is bromine with 1,2-dibromoethane to obtain a compound of formula (V):

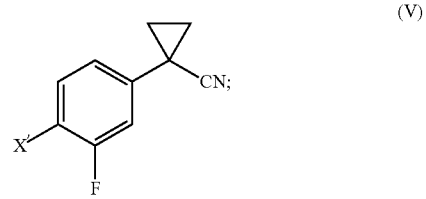

(b) coupling said compound of formula (V) with a compound of formula (VI):

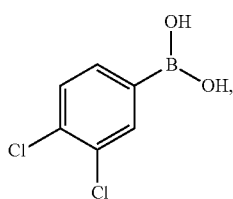

to obtain a compound of formula (VII):

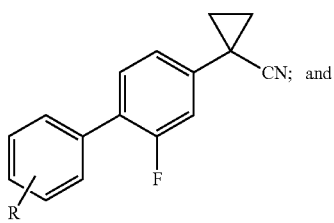

(c) hydrolyzing said compound of formula (VII) to obtain said compound of formula (IA),
wherein said coupling (b) is conducted in the presence of a 1:2 w/w mixture of $Pd(OCOCH_3)_2$ and triphenylphosphine.

2. A process according to claim 1, further comprising isolating and crystallizing said compound of formula (IA).

3. A process according to claim 1, which comprises:
subjecting a compound of formula (II):

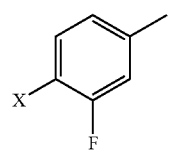

to radical bromination to obtain a compound of formula (III):

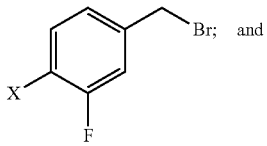

reacting said compound of formula (III) with a cyanide salt to obtain the corresponding nitrile compound of formula (IV).

4. A process according to claim 3, further comprising isolating and crystallizing said compound of formula (IA).

5. A process according to claim 3, wherein said radical bromination is conducted with N-bromosuccinimide in acetonitrile in the presence of a catalytic amount of benzoyl peroxide.

6. A process for preparing a pharmaceutical composition, which comprises:
preparing a compound of formula (IA) by a process according to claim 1; and
combining said compound of formula (IA) with one or more pharmaceutically acceptable excipients.

* * * * *